US00PP20219P2

(12) United States Plant Patent
Smith

(10) Patent No.: US PP20,219 P2
(45) Date of Patent: Aug. 18, 2009

(54) ***CHRYSANTHEMUM* PLANT NAMED 'BRILLIANT YOTIFFANY'**

(50) Latin Name: *Chrysanthemum×morifolium*
Varietal Denomination: Brilliant Yotiffany

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,234

(22) Filed: Jun. 16, 2008

(51) Int. Cl.
*A01H 5/00* (2006.01)

(52) U.S. Cl. ..... Plt./289

(58) Field of Classification Search ..... Plt./289
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Brilliant Yotiffany', characterized by its upright, outwardly spreading and mounding plant habit; freely branching habit; dense and full plant habit; uniform and freely flowering habit; decorative-type inflorescences with bright yellow-colored ray florets; and natural season flowering about September 6$^{th}$ in the Northern Hemisphere.

1 Drawing Sheet

Botanical designation: *Chrysanthemum×morifolium.*
Cultivar denomination: 'BRILLIANT YOTIFFAY'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum*, and hereinafter referred to by the name 'Brilliant Yotiffany'.

The new *Chrysanthemum* is a naturally-occurring whole plant mutation of *Chrysanthemum×morifolium* 'Yotiffany', disclosed in U.S. Plant Pat. No. 17,425. The new *Chrysanthemum* was discovered and selected by the Inventor as a single flowering plant from within a population of plants of 'Yotiffany' in a controlled greenhouse environment in Alva, Fla. November, 2004.

Asexual reproduction of the new *Chrysanthemum* by vegetative cuttings was first conducted in a controlled greenhouse environment in Alva, Fla. in January, 2005. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Brilliant Yotiffany'. These characteristics in combination distinguish 'Brilliant Yotiffany' as a new and distinct garden *Chrysanthemum* cultivar:

1. Upright, outwardly spreading and mounded plant habit.
2. Freely branching habit; dense and full plant habit.
3. Uniform and freely flowering habit.

4. Decorative-type inflorescences.
5. Bright yellow-colored ray florets.
6. Natural season flowering occurs about September 6$^{th}$ in the Northern Hemisphere.

In side-by-side comparisons conducted in Alva, Fla., plants of the new *Chrysanthemum* differed from plants of the parent, 'Yotiffany', in the following characteristics:

1. Plants of the new *Chrysanthemum* were slightly larger than plants of 'Yotiffany'.
2. Plants of the new *Chrysanthemum* flowered two to three days later than plants of 'Yotiffany' when grown under natural season conditions.
3. Plants of the new *Chrysanthemum* and 'Yotiffany' differed in ray floret color as plants of 'Yotiffany' had white-colored ray florets.

Plants of the new *Chrysanthemum* can be compared to plants of *Chrysanthemum×morifolium* 'Yellow Nicole', disclosed in U.S. Plant Pat. No. 8,757. In side-by-side comparisons conducted in Alva, Fla., plants of the new *Chrysanthemum* differed from plants of 'Yellow Nicole' in the following characteristics:

1. Plants of the new *Chrysanthemum* were smaller and more rounded than plants of 'Yellow Nicole'.
2. Plants of the new *Chrysanthemum* flowered more uniformly than plants of 'Yellow Nicole'.
3. Plants of the new *Chrysanthemum* had slightly smaller inflorescences than plants of 'Yellow Nicole'.

Plants of the new *Chrysanthemum* can be compared to plants of *Chrysanthemum×morifolium* 'Gold Crest', disclosed in U.S. Plant Pat. No. 11,606. In side-by-side comparisons conducted in Alva, Fla., plants of the new *Chrysanthemum* differed from plants of 'Gold Crest' in the following characteristics:

1. Plants of the new *Chrysanthemum* were more rounded than plants of 'Gold Crest'.
2. Plants of the new *Chrysanthemum* flowered more uniformly than plants of 'Gold Crest'.
3. Plants of the new *Chrysanthemum* had slightly smaller inflorescences than plants of 'Gold Crest'.

4. Plants of the new *Chrysanthemum* flowered two weeks earlier than plants of 'Gold Crest' when grown under natural season conditions.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Brilliant Yotiffany' grown in a container.

The photograph at the top of the sheet is a close-up view of typical inflorescences of 'Brilliant Yotiffany'.

DETAILED BOTANICAL DESCRIPTION

The aforementioned photographs and following observations and measurements describe plants grown in Alva, Fla. during the late spring and summer in a polycarbonate-covered greenhouse and under conditions and practices which approximate those generally used in commercial garden *Chrysanthemum* production. During the production of the plants, day temperatures averaged 32° C. and night temperatures averaged 21° C. Plants were grown in 15-containers under short day/long night conditions. Plants were ten weeks from planting when the photographs and description were taken. In the following description, color references are made to The Royal Horticultural Society Colour Chart, 1995 Edition, except where general terms of ordinary dictionary significance are used.

Botanical classification: *Chrysanthemum×morifolium* 'Brilliant Yotiffany'.

Parentage: Naturally-occurring whole plant mutation of *Chrysanthemum×morifolium* 'Yotiffany', disclosed in U.S. Plant Pat. No. 17,425.

Propagation:

*Type.*—Terminal vegetative cuttings.

*Time to initiate root.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial decorative-type garden *Chrysanthemum*. Stems upright and outwardly spreading giving a uniformly mounded appearance to the plant. Freely branching habit, about five lateral branches each with multiple secondary branches; pinching is not required; dense and full plant habit. Strong and vigorous growth habit.

*Plant height.*—About 19.5 cm.

*Plant width.*—About 27 cm.

*Lateral branches.*—Length: About 17 cm. Diameter: About 4 mm. Internode length: About 9 mm. Strength: Strong. Texture: Pubescent; longitudinally ridged. Color: Close to 146B.

*Leaves.*—Arrangement: Alternate, simple. Length: About 4.5 cm. Width: About 3 cm. Apex: Acute to mucronate. Base: Attenuate. Margin: Palmately lobed, sinuses between lateral lobes mostly parallel. Texture, upper and lower surfaces: Pubescence; veins prominent on lower surface. Color: Developing foliage, upper surface: Close to 147A. Developing foliage, lower surface: Close to 147B. Fully expanded foliage, upper surface: Close to 137A; venation, close to 147C. Fully expanded foliage, lower surface: Close to 147B; venation, close to 147B. Petiole: Length: About 1.5 cm. Diameter: About 2.5 mm. Texture, upper and lower surfaces: Pubescent. Color, upper and lower surfaces: Close to 146B.

Inflorescences description:

*Appearance.*—Decorative-type inflorescence form with lanceolate to narrowly oblanceolate-shaped ray florets. Inflorescences borne on terminals above foliage. Disc and ray florets arranged acropetally on a capitulum. Inflorescences fragrant, pungent.

*Flowering response.*—Under natural season conditions, plants flower about September 6$^{th}$ in the Northern Hemisphere.

*Postproduction longevity.*—Inflorescences maintain good color and substance for about four weeks in an outdoor nursery. Inflorescences persistent.

*Quantity of inflorescence.*—About 34 inflorescences develop per lateral branch.

*Inflorescence bud.*—Height: About 1.2 cm. Diameter: About 1.4 cm. Shape: Oblate. Color: Close to 11C.

*Inflorescence size.*—Diameter: About 4 cm. Depth (height): About 1.4 cm. Disc diameter: About 2 mm. Receptacle diameter: About 2 cm. Receptacle height: About 6 mm. Receptacle color: Close to 147B.

*Ray florets.*—Shape: Lanceolate to narrowly oblanceolate; partially quilled. Orientation: Initially upright, then about 90° from vertical. Aspect: Initially incurved, then mostly flat; apices curved upwardly. Length: About 2.1 cm. Width: About 3.5 mm. Apex: Emarginate. Base: Acute. Margin: Entire. Texture, upper and lower surfaces: Smooth, glabrous; velvety; longitudinally ribbed. Number of ray florets per inflorescence: About 180 arranged in about 12 to 13 whorls. Color: When opening, upper surface: Close to 11A. When opening, lower surface: Close to 11B. Fully opened, upper surface: Close to 12A; color does not fade with development. Fully opened, lower surface: Close to 11B; color does not fade with development.

*Disc florets.*—Shape: Tubular, elongated. Length: About 1.5 mm. Diameter: Less than 1 mm. Number of disc florets per inflorescence: About three to five. Color, immature and mature: Apex: Close to 12C. Mid-section: Close to 12D. Base: Close to 157D.

*Phyllaries.*—Number of phyllaries per inflorescence: About 28 arranged in about three whorls. Length: About 6 mm. Width: About 2.5 mm. Shape: Lanceolate. Apex: Acute. Base: Truncate. Texture, upper surface: Smooth, glabrous. Texture, lower surface: Pubescent. Color, upper surface: Close to 146A. Color, lower surface: Close to 146B.

*Peduncles.*—Length, terminal peduncle: About 4.4 cm. Length, fourth peduncle: About 3.7 cm. Diameter, terminal peduncle: About 2 mm. Angle: Mostly upright to 30° to 40° from vertical. Strength: Strong. Texture: Pubescent. Color: Close to 148B.

*Reproductive organs.*—Androecium: Not observed. Gynoecium: Pistil length: About 6 mm. Stigma shape: Bi-parted. Stigma color: Close to 2A. Style length: About 4 mm. Style color: Close to 1C. Ovary color: Close to 157D.

*Seed/fruit.*—Seed and fruit production has not been observed.

Disease/pest resistance: Resistance to pathogens and pests common to *Chrysanthemum* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Brilliant Yotiffany' as illustrated and described.

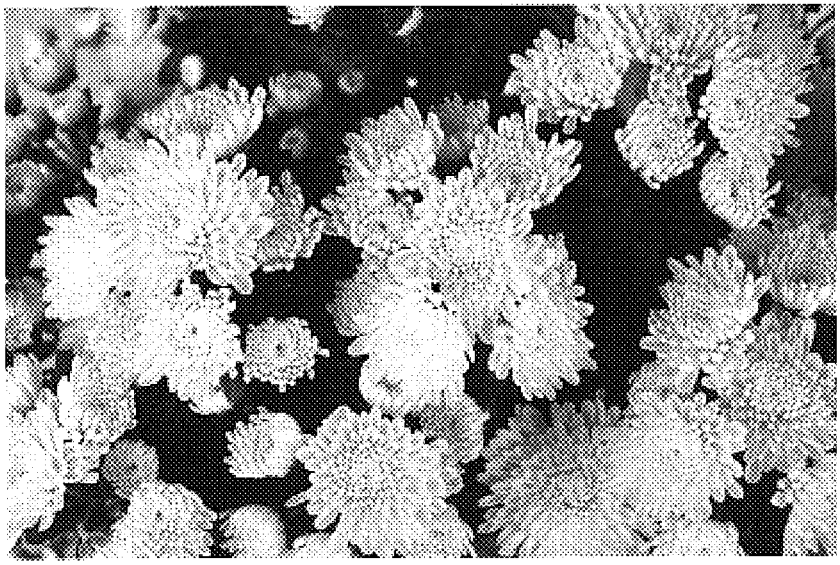
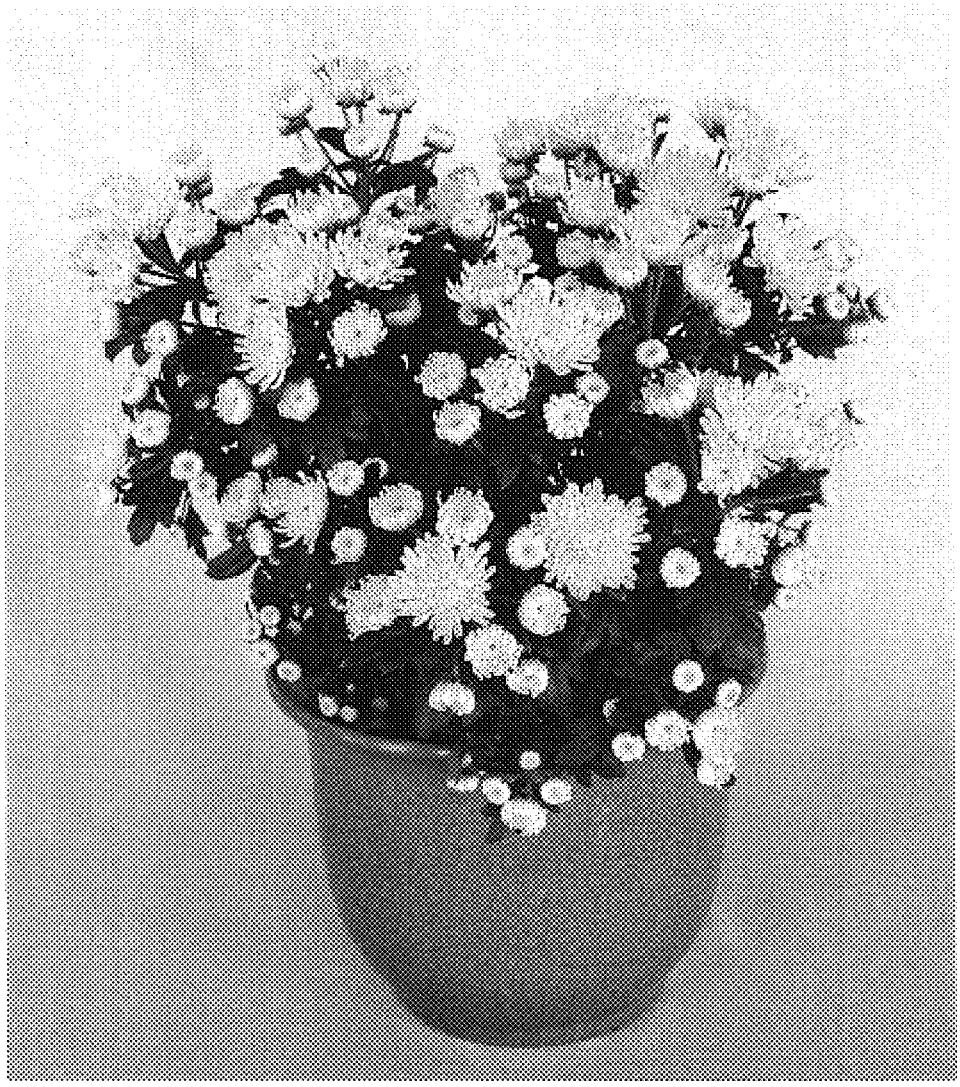

* * * * *